(12) United States Patent
Kramer et al.

(10) Patent No.: US 9,968,466 B2
(45) Date of Patent: May 15, 2018

(54) PROSTHETIC FOOT WITH PROGRAMMABLE MOVEMENT

(71) Applicant: Tai Lore Made, LLC, Orlando, FL (US)

(72) Inventors: Leslie D. Kramer, Orlando, FL (US); William Stanley Patterson, Orlando, FL (US)

(73) Assignee: Tai Lore Made, LLC, Orlando, FL (US)

( * ) Notice: Subject to any disclaimer, the term of this patent is extended or adjusted under 35 U.S.C. 154(b) by 78 days.

(21) Appl. No.: 15/053,652

(22) Filed: Feb. 25, 2016

(65) Prior Publication Data

US 2016/0175119 A1   Jun. 23, 2016

Related U.S. Application Data

(63) Continuation-in-part of application No. 14/942,405, filed on Nov. 16, 2015, now Pat. No. 9,844,449,
(Continued)

(51) Int. Cl.
| | |
|---|---|
| *A61F 2/66* | (2006.01) |
| *A61F 2/70* | (2006.01) |
| *A61F 2/76* | (2006.01) |
| *A61F 2/50* | (2006.01) |
| *A61F 2/68* | (2006.01) |
| *A61F 2/74* | (2006.01) |

(52) U.S. Cl.
CPC .............. *A61F 2/66* (2013.01); *A61F 2/6607* (2013.01); *A61F 2/68* (2013.01); *A61F 2/76* (2013.01);
(Continued)

(58) Field of Classification Search
CPC .. A61F 2/60; A61F 2/66; A61F 2/6607; A61F 2/68; A61F 2/76; A61F 2/78;
(Continued)

(56) References Cited

U.S. PATENT DOCUMENTS

| | | |
|---|---|---|
| 2,464,391 A | 3/1949 | Havens |
| 2,475,372 A | 7/1949 | Catranis |
| | (Continued) | |

FOREIGN PATENT DOCUMENTS

| | | |
|---|---|---|
| DE | 327423 | 10/1920 |
| DE | 818828 | 10/1951 |
| | (Continued) | |

OTHER PUBLICATIONS

Daniel Rihs, Ivan Polizzi: "Prosthetic Foot Design"; Rehab Tech, Monash Rehabilitation Technology Unit, Victorian University of Technology, Final Year Project, 1996.
(Continued)

*Primary Examiner* — Thomas J Sweet
*Assistant Examiner* — Christie Bahena
(74) *Attorney, Agent, or Firm* — Christopher M. Ramsey; GrayRobinson, P.A.

(57) ABSTRACT

A programmable prosthetic foot includes a heel member simulating a heel portion of a human foot. The heel member has an elongated heel member shaft extending in a vertical direction. The foot also includes a forefoot member simulating a forefoot portion of a human foot. The forefoot member has an elongated forefoot member shaft extending in the vertical direction. A sensor on the foot detects compressive force on the heel member shaft and/or forefoot member shaft during a step. An actuator on the foot imparts vertical translation to the heel member shaft and/or forefoot member shaft. An electronic controller in operable communication with the actuator includes program instructions for operating the actuator by imparting the vertical translation to the heel member shaft and/or forefoot member shaft as a function of the compressive force detected by the sensor.

8 Claims, 7 Drawing Sheets

Related U.S. Application Data which is a continuation of application No. 14/499,603, filed on Sep. 29, 2014, now Pat. No. 9,186,264, which is a continuation of application No. 14/051,746, filed on Oct. 11, 2013, now Pat. No. 8,876,913.

(60) Provisional application No. 61/712,981, filed on Oct. 12, 2012.

(52) U.S. Cl.
CPC . *A61F 2002/502* (2013.01); *A61F 2002/5003* (2013.01); *A61F 2002/503* (2013.01); *A61F 2002/5007* (2013.01); *A61F 2002/5083* (2013.01); *A61F 2002/5086* (2013.01); *A61F 2002/665* (2013.01); *A61F 2002/6614* (2013.01); *A61F 2002/6642* (2013.01); *A61F 2002/6664* (2013.01); *A61F 2002/6678* (2013.01); *A61F 2002/701* (2013.01); *A61F 2002/704* (2013.01); *A61F 2002/705* (2013.01); *A61F 2002/74* (2013.01); *A61F 2002/7635* (2013.01)

(58) Field of Classification Search
CPC ...... A61F 2002/5001; A61F 2002/5003; A61F 2002/5007; A61F 2002/5009; A61F 2002/502; A61F 2002/503; A61F 2002/5081; A61F 2002/509; A61F 2002/6614; A61F 2002/6621; A61F 2002/6628; A61F 2002/6635; A61F 2002/6642; A61F 2002/665; A61F 2002/6657; A61F 2002/6671; A61F 2002/6678; A61F 2002/6685; A61F 2002/6692; A61F 3/00; B25J 9/0006
See application file for complete search history.

(56) References Cited

U.S. PATENT DOCUMENTS

| | | | |
|---|---|---|---|
| 3,551,914 A | 1/1971 | Woodall | |
| 4,370,761 A | 2/1983 | Serri | |
| 4,547,913 A | 10/1985 | Phillips | |
| 5,376,133 A | 12/1994 | Gramnas | |
| 5,653,768 A | 8/1997 | Kania | |
| 5,766,264 A | 6/1998 | Lundt | |
| 5,800,563 A | 9/1998 | Arbogast et al. | |
| 6,083,265 A | 7/2000 | Shorter et al. | |
| 6,129,766 A | 10/2000 | Johnson et al. | |
| 6,139,550 A | 10/2000 | Michelson | |
| 6,406,500 B1 | 6/2002 | Phillips | |
| 7,815,682 B1 | 10/2010 | Peterson et al. | |
| 7,862,622 B2 | 1/2011 | Dunlap et al. | |
| 7,867,285 B2 | 1/2011 | Clausen et al. | |
| D655,009 S | 2/2012 | L'Heureux et al. | |
| 8,317,877 B2 | 11/2012 | Doddroe et al. | |
| 8,876,913 B2 | 11/2014 | Kramer et al. | |
| 2002/0143408 A1 | 10/2002 | Townsend et al. | |
| 2006/0069448 A1* | 3/2006 | Yasui | A61F 2/60 623/24 |
| 2007/0050045 A1* | 3/2007 | Clausen | A61F 2/66 623/24 |
| 2009/0265018 A1* | 10/2009 | Goldfarb | A61F 2/60 623/40 |
| 2012/0134742 A1 | 5/2012 | Changsrivong et al. | |
| 2012/0271434 A1 | 10/2012 | Friesen et al. | |
| 2013/0066439 A1 | 3/2013 | Zamora et al. | |
| 2013/0173023 A1 | 7/2013 | Lecomte et al. | |
| 2015/0018976 A1 | 1/2015 | Kramer et al. | |

FOREIGN PATENT DOCUMENTS

| | | |
|---|---|---|
| GB | 114385 | 4/1918 |
| JP | 2009521290 A | 6/2009 |

OTHER PUBLICATIONS

International Search Report dated Feb. 6, 2014 for PCT/US2013/064492.
Office Action dated Apr. 24, 2015 for U.S. Appl. No. 14/499,603.
Office Action dated Aug. 1, 2014 for U.S. Appl. No. 14/051,746.
Office Action dated Aug. 5, 2015 for U.S. Appl. No. 14/349,019.
Office Action dated Jul. 3, 2014 for U.S. Appl. No. 14/051,746.
Office Action dated Dec. 16, 2016 for U.S. Appl. No. 14/942,405.
Office Action dated Jul. 4, 2017 for U.S. Appl. No. 14/942,405.

* cited by examiner

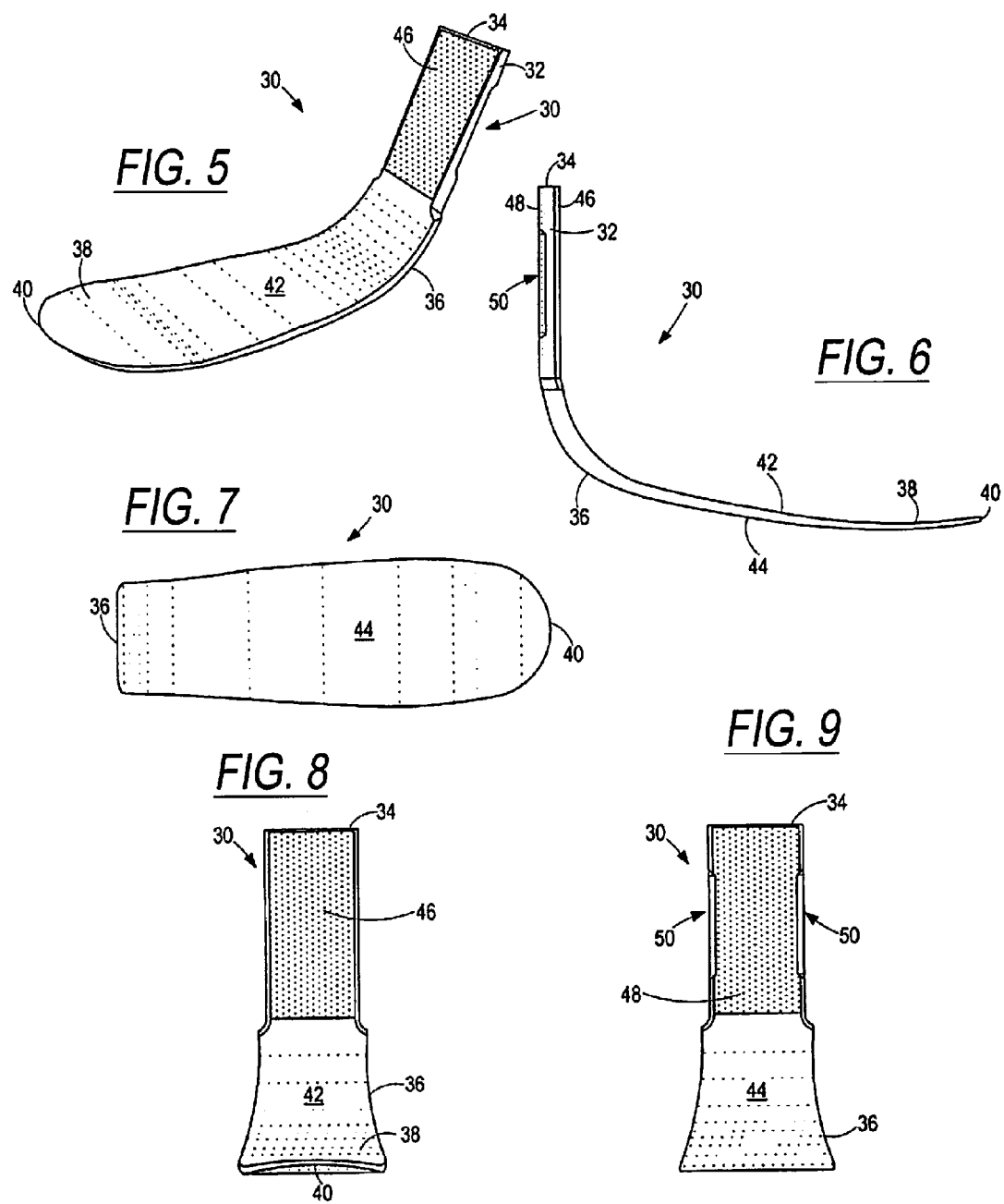

PROSTHETIC FOOT WITH PROGRAMMABLE MOVEMENT

CROSS-REFERENCE TO RELATED APPLICATIONS

This is a continuation-in-part of application Ser. No. 14/942,045, filed Nov. 16, 2015, which is a continuation of application Ser. No. 14/499,603, filed Sep. 29, 2014, which is a continuation of application Ser. No. 14/051,746, filed Oct. 11, 2013, which claims priority to U.S. provisional Application No. 61/712,981, filed Oct. 12, 2012. This also claims priority to provisional Application No. 62/126,781, filed Mar. 2, 2015. These priority documents are incorporated by reference in their entireties.

FIELD

This relates to the field of prosthetics and, more particularly, to prosthetic feet.

BACKGROUND

Conventional prosthetic feet are not easily adaptable for use with a broad range of activities. Prosthetic foot users must choose from a variety of different prosthetic feet, each of which is optimized for a different situation such as walking, running, dancing, etc. A conventional prosthetic foot designed for routine day-to-day activities is not optimized for performing more vigorous exercise. For this reason, many prosthetic foot users will wear different prosthetic feet for different activities.

Conventional prosthetic feet are not easily adaptable to different environmental conditions either. In contrast to a natural foot, most prosthetic feet will provide the same degree of heel and forefoot movement because these components are generally bonded or bolted together regardless of the terrain. For example, the movements a natural foot makes when walking on a flat surface are completely different than the movements it makes when walking on stairs or running.

BRIEF SUMMARY

In view of the drawbacks associated with conventional prosthetic feet, it would be advantageous to have a prosthetic foot with electronically adjustable heel and forefoot movements and a control system for controlling those movements.

Such a programmable prosthetic foot includes a heel member simulating a heel portion of a human foot. The heel member has an elongated heel member shaft extending in a vertical direction. The foot also includes a forefoot member simulating a forefoot portion of a human foot. The forefoot member has an elongated forefoot member shaft extending in the vertical direction. A sensor on the foot detects compressive force on the heel member shaft and/or forefoot member shaft during a step. An actuator on the foot imparts vertical translation to the heel member shaft and/or forefoot member shaft. An electronic controller in operable communication with the actuator includes program instructions for operating the actuator by imparting the vertical translation to the heel member shaft and/or forefoot member shaft as a function of the compressive force detected by the pressure sensor.

An associated system for controlling the movement of a prosthetic foot includes at least one actuator capable of extending and retracting. The at least one actuator is in operable contact with a heel member simulating a heel portion of a human foot and/or a forefoot member simulating a forefoot portion of a human foot to cause the heel member shaft and/or forefoot member shaft to translate in a vertical direction. At least one sensor is positioned so as to detect compressive force applied to the actuator. Machine readable memory stores a plurality of datasets corresponding to heel member and forefoot member positions during a human step. An electronic controller is connected to the sensor and actuator in such a way that the controller receives a signal corresponding to the detected compressive force and adjusts the extension or retraction of the actuator based on at least one of the datasets.

A method of controlling the movement of a prosthetic foot having independent heel and forefoot members respectively simulating a heel and a forefoot portion of a wearer's foot includes detecting a compressive force applied to the heel member and/or forefoot member during a wearer's step and receiving, by an electronic controller, a signal corresponding to the detected compressive force. A dataset corresponding to a heel member and forefoot member positions during the wearer's step is retrieved from machine readable memory. The degree of extension of an actuator in operable communication with the controller is adjusted based on the dataset, thereby causing the heel member and/or forefoot member to translate in a vertical direction while the wearer takes a step.

BRIEF DESCRIPTION OF THE DRAWINGS

FIG. 5 is a side anterior perspective view of an exemplary forefoot member useful with the prosthetic foot of FIG. 1.

FIG. 6 is a side elevation of the forefoot member of FIG. 5.

FIG. 7 is a bottom view of the forefoot member of FIG. 5;

FIG. 8 is an anterior elevation view of the forefoot member of FIG. 5.

FIG. 9 is a posterior elevation view of the forefoot member of FIG. 5.

DETAILED DESCRIPTION OF EXAMPLE EMBODIMENTS

Figure 1:
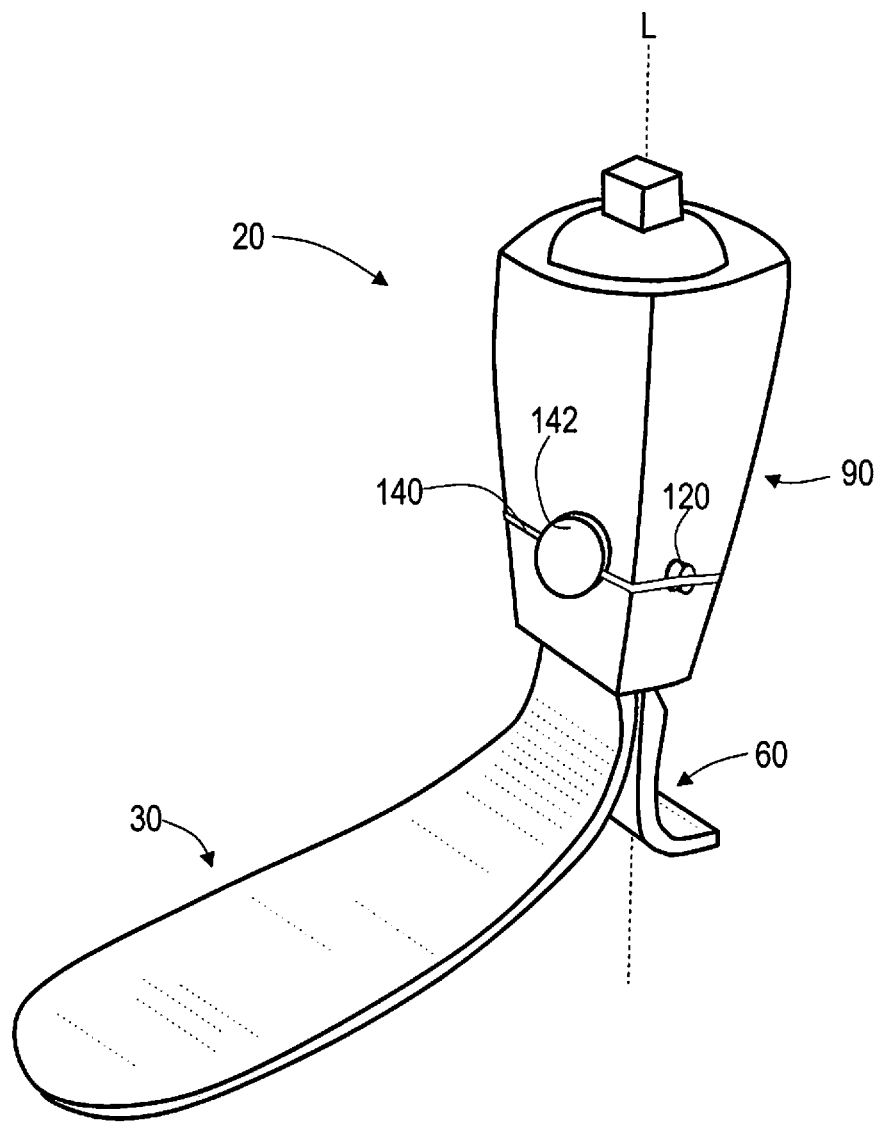
FIG. 1 is a side anterior perspective view of an exemplary embodiment of the prosthetic foot.

FIG. 1 generally illustrates an exemplary embodiment of the prosthetic foot 20. The foot 20 includes a forefoot member 30, a heel member 60, and an ankle member 90. In practice, the foot 20 is attached to a limb connector 130 designed to connect the foot to the wearer's leg. The wearer's leg defines a vertical axis L along which the ankle member 90 is aligned. The foot 20 may function regardless of the type of limb connector 130 used.

The prosthetic foot 20 is modular and includes parts that can be removed and substituted very easily to meet the individual needs of the wearer. This allows the components to be interchanged with other components for the purpose of replacement or for the purpose of substituting one component for another component having different properties. For example, the original forefoot and heel members may be interchanged with different forefoot and heel members suited to a particular activity, the wearer's gait, the wearer's lifestyle, a particular shoe size, the wearer's height, or the wearer's weight.

Figure 2:
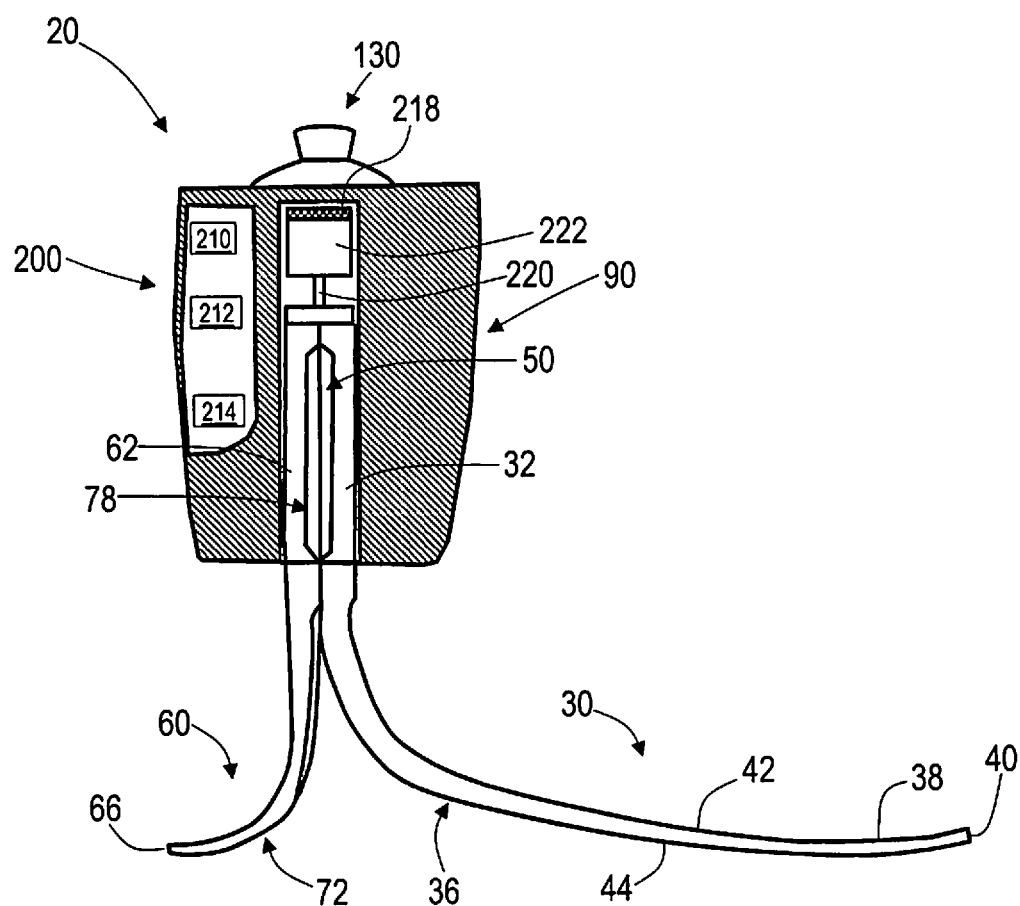
FIG. 2 is a side view thereof with a lateral side of the ankle member cutaway.
Figure 3:
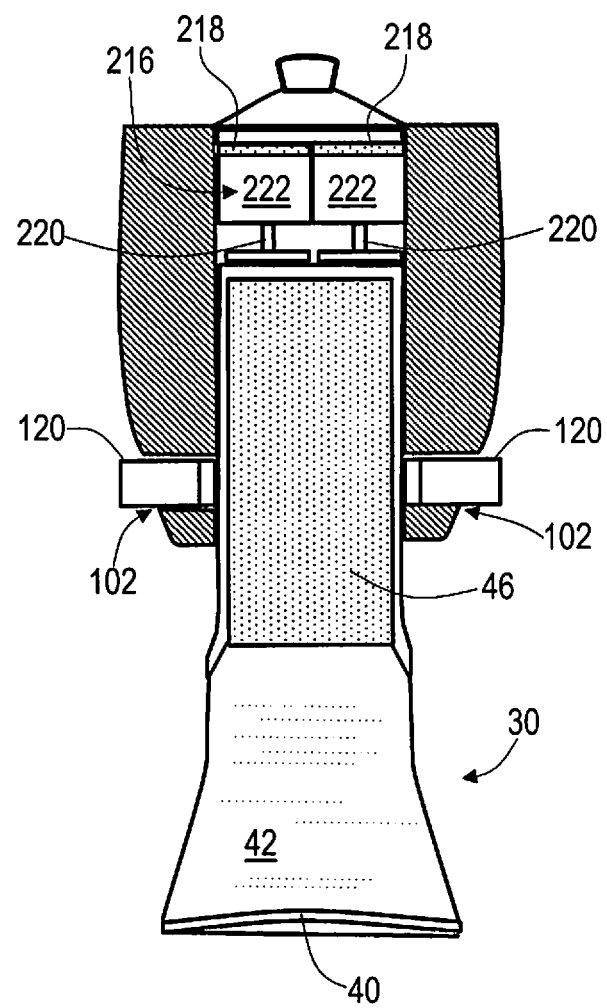
FIG. 3 is a front view thereof with the anterior side of the ankle member cutaway.

In FIGS. 2 and 3 the facing side of the ankle member 90 is cut away so that the mechanical functionality of various components is revealed. Details of each component are discussed in turn.

The ankle member 90 forms a sleeve into which a forefoot member shaft 32 and heel member shaft 62 are positioned. The ankle member 90 applies inward force against the forefoot member shaft 32 and heel member shaft 62 to maintain alignment of the respective shafts 32, 62 along the vertical axis of the ankle member 90. The forefoot member shaft 32 and heel member shaft 62 slide independently along the ankle member when the user takes a step 60.

Figure 4:
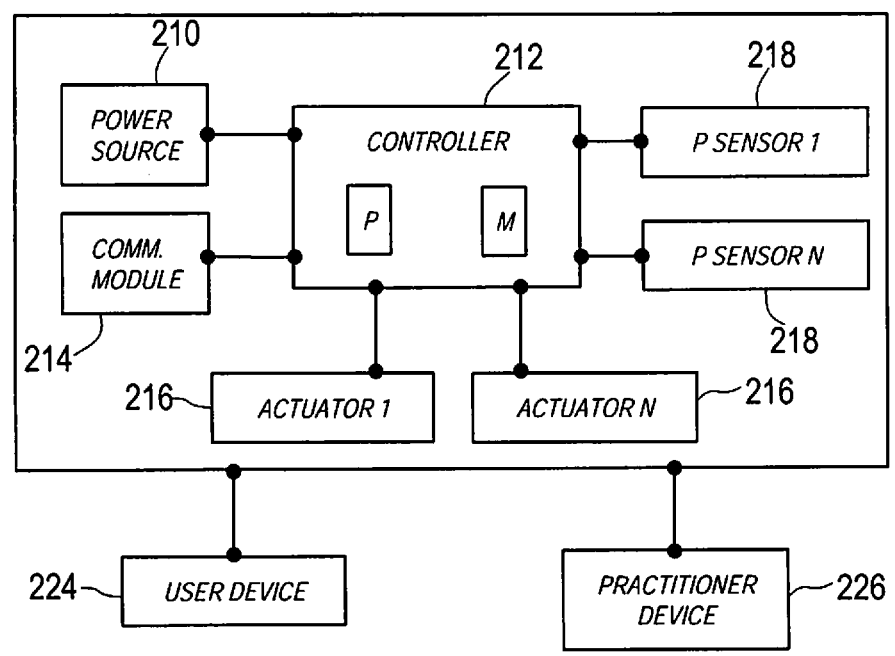
FIG. 4 is a block diagram showing aspects of an exemplary prosthetic foot control system.
Figure 10:
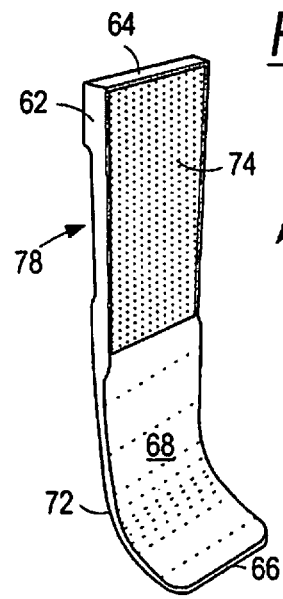
FIG. 10 is a side posterior perspective view of an exemplary heel member useful with the prosthetic foot of FIG. 1.
Figure 11:
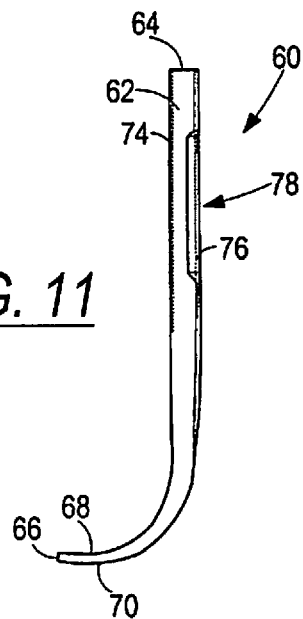
FIG. 11 is a side elevation view of the heel member of FIG. 10.
Figure 12:
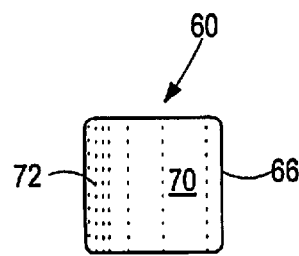
FIG. 12 is a bottom view of the heel member of FIG. 10.
Figure 13:
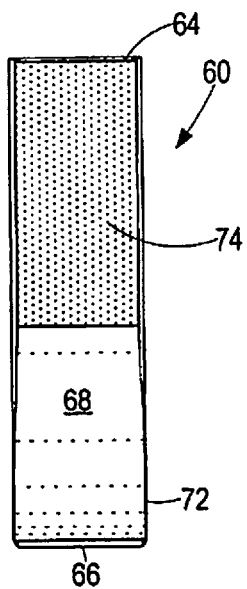
FIG. 13 is a posterior elevation view of the heel member of FIG. 10.
Figure 14:
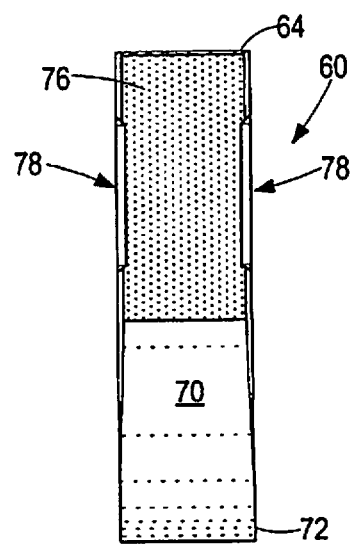
FIG. 14 is an anterior elevation view of the heel member of FIG. 10.
Figure 15:
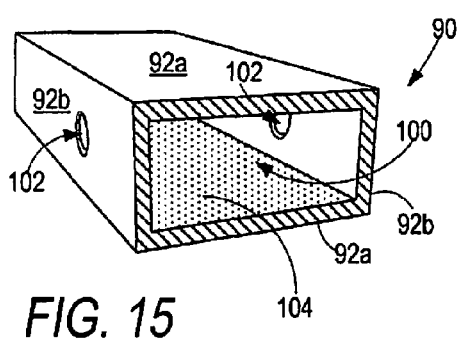
FIG. 15 is a bottom perspective view of an exemplary ankle member useful with the prosthetic foot of FIG. 1.
Figure 16:
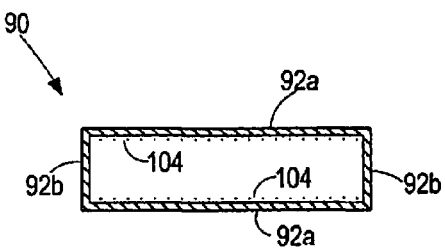
FIG. 16 is a bottom view of the ankle member of FIG. 15.
Figure 17:
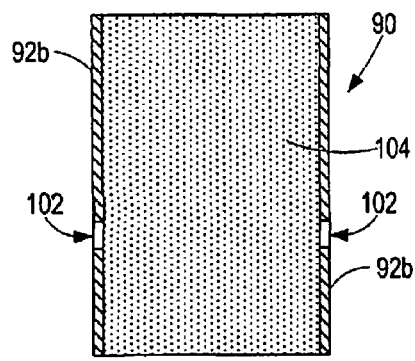
FIG. 17 is anterior or posterior side elevation view of the ankle member of FIG. 15 with the facing side cutaway.
Figure 18:
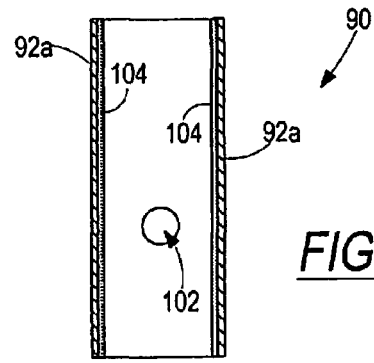
FIG. 18 is a lateral side elevation view of the ankle member of FIG. 15 with the facing side cutaway.
Figure 19:
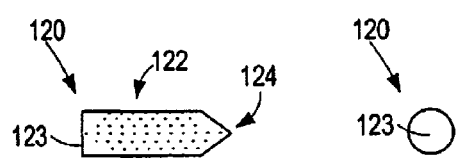
FIG. 19 is a side elevation view of an exemplary pin useful with the prosthetic foot of FIG. 1.
Figure 21:
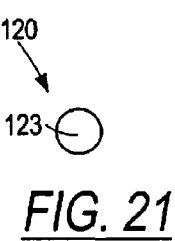
FIG. 21 is a rear elevation view of the pin of FIG. 19.
Figure 20:
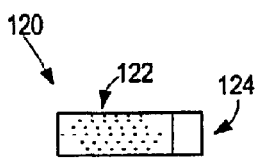
FIG. 20 is a top or bottom view of the pin of FIG. 19.
Figure 22:
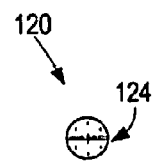
FIG. 22 is a front elevation view of the pin of FIG. 19.

Referring to FIGS. 2 to 4, the movement of the forefoot member and heel member shafts 32,62 is controlled by a control system 200, including a power source 210, a controller 212, a communication module 214, at least one actuator 216, and at least one pressure sensor 218. The power source 210, controller 212, and communication module 214 are mounted on the ankle member 90.

The power source 210 is an electric device capable of powering the controller 212, a communication module 214, at least one actuator 216, and at least one pressure sensor 218. A preferred power source 210 is a battery, such as a lithium-ion battery for example, or the like.

The controller 212 includes a CPU with a processor P and memory M. The processor P executes machine readable instructions stored on the memory M. The controller 212 also includes I/O circuitry for sending and receiving signals to/from the communication module 214, actuator(s) 216, and pressure sensor(s) 218.

The communication module 214 is an electronic device adapted to communicate with external communications devices such as computers, tablets, smart phones, or the like via a network such as the Internet. The communication module 214 is able to send signals to and receive signals from these external devices, preferably via a wireless link, which may include wi-fi and/or Bluetooth-type link.

The number of actuators 216 employed will depend on manufacturer technology to fit the space available, and/or wearer preferences. The block diagram in FIG. 4 refers to Actuator 1 and Actuator N. Here, N signifies that N number of actuators may be employed. In the embodiment shown in FIG. 4, two actuators 216 are shown by way of example.

The actuator 216 includes an axial ram 220 that extends and retracts from an actuator body 222. The degree and timing of the extension and retraction is controlled by the controller 212 based on instructions stored on the memory M. Examples of actuators 216 that may be used include: electromechanical actuators, hydraulic actuators, pneumatic actuators, solenoids, piezoelectric actuators, and the like. In a preferred example the actuators 216 have a stroke length of about 0.25 inches to about 1.25 inches, about 0.25 inches to about 0.75 inches, or about 0.5 inches and has an extension/retraction time of about 1 to about 1000 milliseconds.

A pressure sensor 218 is mounted at the top of each actuator 216 and detects pressure or force exerted thereon when the wearer takes a step. The detected force or pressure data are provided via the I/O circuitry to the controller 212. Examples of pressure sensors 218 that may be used include capacitive pressure sensors, mechanical pressure sensors, and the like.

The pressure sensor 218 detects the local pressure or force generated at an actuator 216. The pressure/force signal is sent to the controller 212, which registers the signal and the time it arrived. This allows the controller 216 to store on the memory M data associated with the wearer's gait as force or pressure amplitude vs. time. This feature allows the extension and retraction profile of the actuators 216 to be customized to the wearer's gait. By way of example, the memory M may include a plurality of different amplitude vs. time datasets, each representing a different type of movement, such as walking, running, jumping, walking backwards, walking on stairs, traversing inclines, and traversing declines, among many other examples.

The wearer may communicate with the control system 200 via a user device 224, which is an electronic device such as a computer, tablet, smart phone or the like that can communicate via the network. The wearer may adjust the movement of the actuators 216 by inputting the desired characteristics at the user device 224. The user device 224 then transmits the wearer's instructions to the control system 200. This allows the wearer to dynamically adjust the actuators 216 to the wearer's preferences without exchanging any of the components. For example, if the wearer intends to walk up a flight of stairs, the wearer may, via the user device 224, instruct the control system 200 to adjust the actuators 216 for walking up the stairs. The processor P may execute the instructions by selecting the appropriate dataset from the memory M.

When upward force acts on the heel member 60 or forefoot member 30 during the wearer's step, the respective shaft 32, 62 is able to slide vertically within the ankle member 90 and push against the actuator(s) 216. This force is detected by the pressure sensor(s) 218. The heel member shaft 62 and forefoot member shaft 32 slide independently of one another along the ankle member 90 because, in the example shown, the mechanical link between the shafts 32, 62 is simply the inward force applied by ankle member 90.

The heel member 60 can easily be removed from the ankle member 90 by sliding it out of the ankle member 90. Likewise, the forefoot member 32 can easily be removed from the ankle member 90 by sliding it out of the ankle member 90. Either of these components can then be replaced with a different heel member 60 and/or forefoot member 30 that suits a certain activity or weight without needing to remove the ankle member 90 from the wearer's limb. This also allows worn components to be replaced without needing to replace the entire foot or send the foot back to the manufacturer for repair.

Additional details of a preferred forefoot member 30 are shown in FIGS. 5-9. The forefoot member 30 includes the forefoot member shaft 32 and extends from a forefoot member upper end 34 through a curved forefoot section 36 to a toe section end 38 and terminates at a toe end 40. A forefoot member top surface 42 and forefoot member bottom surface 44 are positioned on opposite sides.

At the shaft section 32, the forefoot member top surface 42 includes a lubricated forefoot member anterior surface 46. Also at the shaft section 32, the forefoot member bottom surface 44 includes a lubricated forefoot member posterior surface 48.

The opposed lateral sides of the forefoot member each include an elongated depression 50 formed along the shaft 32 adjacent to the lubricated forefoot member posterior surface 48.

Additional details of a preferred heel member 60 are shown in FIGS. 10-14. The heel member 60 includes the heel member shaft 62 and extends from a heel member upper end 64 through a curved heel section 72 to a heel end 66. A heel member top surface 68 and heel member bottom surface 70 are positioned on opposite sides.

At the shaft section 62, the heel member top surface 68 includes a lubricated heel member posterior surface 74. Also at the shaft section 62, the heel member bottom surface 70 includes a lubricated heel member anterior surface 76.

The opposed lateral sides of the heel member 60 each include an elongated depression 78 formed along the shaft 62 adjacent to the lubricated heel member anterior surface 76.

Additional details of a preferred ankle member 90 are shown in FIGS. 15-18. The ankle member 90 forms a sleeve having opposed anterior and posterior sidewalls 92*a* and opposed lateral side walls 92*b* that together define an interior 100. The interior surface along the anterior and posterior sidewalls 92*a* is lubricated to form anterior and posterior lubricated sidewalls 104. In the embodiment shown, the ankle member 90 is symmetric about a vertical plane bisecting the anterior and posterior sidewalls 92*a* and a vertical plane bisecting the lateral side walls 92*b*.

Both lateral sidewalls 92*b* define a respective opening 102 that passes through to the interior 100. The purpose of the openings 102 is described in detail below.

When the forefoot member 30 and heel member 60 are coupled to the ankle member 90 the lubricated posterior heel member surface 74 is in slidable contact with the ankle member posterior lubricated sidewall 104, the lubricated anterior forefoot member surface 46 is in slidable contact with the ankle member anterior lubricated sidewall 104, and the lubricated posterior forefoot member surface 48 is in slidable contact with the lubricated anterior heel member surface 76.

The lubricated surfaces are preferably formed from a solid lubricating material inlaid into the material that makes up the respective component part. The lubricating material allows the surfaces to slide quietly against each other with little wear. A particularly preferred lubricating material is polytetrafluoroethylene, commonly sold under the name TEFLON® by E.I. DuPont de Nemours and Company, Corp. Other suitable lubricating materials include, but are not limited to other families of fluoropolymers, polyethylene polymers of various molecular weights, acetal resins (commonly sold under the name DELRIN® by E.I. DuPont de Nemours and Company, Corp), or any other polymer that has good resistance to wear due to sliding.

Although not preferable, if desired, a liquid or gel-type lubricant can be applied to the lubricated surfaces for extra lubrication. One must be careful, however, in choosing the lubricant because grit trapped in the lubricant may damage the solid lubricating material.

As shown in FIGS. 1 and 3, pins 120 are positioned through the opposed lateral sidewalls 92*b* of the ankle member 90. Preferred pins 120 are shown in greater detail in FIGS. 20-23. Each pin 120 includes a cylindrical body 122 extending from a first end 123 to a wedge shaped second end 124. The pins 120 are preferably made from the same lubricating material as the lubricated surfaces, most preferably polytetrafluoroethylene, to allow the wedge shaped second end 124 to slide easily against the heel member 90 and forefoot member 30.

As best shown in FIG. 2, within the ankle member 90, the respective depressions 50, 78 of the forefoot member 30 and heel member 60 meet to form a pair of vertical guide slots that define the sliding direction in which the forefoot member 30 and heel member 60 slide.

As best shown in FIG. 3, the pins 120 are positioned through the openings 102 in the ankle member 90 so that the wedge shaped second end 124 of each pin 102 fits within a respective guide slot. The pins 120 restrict the distance the forefoot member 30 and heel member 90 can slide to the length of the guide slots.

As mentioned above, the various components of the prosthetic foot 20 can easily be removed from the ankle member 90 without removing the ankle member 90 from the wearer's leg. This is advantageous for many reasons, some of which have already been described.

It may be useful to include a pin securing member 140 to maintain the position of the pins 120. In the example shown, the pin securing member 140 is an annular strap that extends completely around the ankle member 90 and presses inwardly on the pins 120. In the example shown, the tightness may be adjusted by manipulating a tension controller 142. There are many different strap-type pin securing members 140 that are suitable, including resilient straps that can be stretched over the pins 120 or belt-like straps that include a fastener for joining two ends together. Another example of a preferred pin securing member 140 is a belt-like strap with a hook and loop type fastener.

When used, the pin securing member 140 is preferably tightened around the pins 120 to prevent the pins from sliding out of the openings 102 while pressing the second end 124 of the pins 120 into the guide slots, which, in turn, causes the anterior lubricious surface 46 of the forefoot member and the posterior lubricious surface 74 of the heel member 90 to press against the lubricious surfaces 104 on the interior of the ankle member 90.

The prosthetic foot 20 may be made from any material suitable for making components parts of prosthetic devices and that can allow each of the components to perform its desired functions. The forefoot member 30, heel member 60, and ankle member 90 may be primarily made of the same or a different material. A particularly preferred material for making the forefoot member 30, heel member 60, and ankle member 90 is carbon fiber composite because it is lightweight, strong, and resilient. The properties of carbon fiber are also tunable to meet a desired need by varying the ply schedule, layer orientation, resins, and fabrication process employed to make each part.

The scope of the components is not limited to the particular shape of the examples shown in the drawings and described. The shape of each component may vary to account for a wearer's activity level and/or weight or may vary to be suited to a particular activity such as running.

This disclosure describes example embodiments, but not all possible embodiments of the prosthetic foot. Where a particular feature is disclosed in the context of a particular embodiment, that feature can also be used, to the extent possible, in combination with and/or in the context of other embodiments. The prosthetic foot be embodied in many different forms and should not be construed as limited to only the embodiments described here.

That which is claimed is:

1. A prosthetic foot comprising:
 a heel member forming a heel portion of the prosthetic foot, the heel member including an elongated heel member shaft extending in a vertical direction;
 a forefoot member forming a forefoot portion of the prosthetic foot, the forefoot member including an elongated forefoot member shaft extending in the vertical direction;
 a sensor that can detect compressive force on the heel member shaft and/or forefoot member shaft during a step;
 an actuator that can impart vertical translation to the heel member shaft and/or forefoot member shaft; and
 an electronic controller in operable communication with the actuator, the electronic controller including program instructions for operating the actuator by imparting the vertical translation to the heel member shaft and/or forefoot member shaft as a function of the compressive force detected by the sensor;
 wherein:
  the heel member shaft is a rigid single piece that extends from an upper end received by an ankle member to a lower end positioned beneath the ankle member; and
  the forefoot member shaft is a rigid single piece that extends from an upper end received by the ankle member to a lower end positioned beneath the ankle member.

2. The prosthetic foot of claim 1, further comprising a user communication device in wireless communication with the electronic controller and wherein the electronic controller includes a plurality of different program instructions for different types of human steps and the different program instructions are selectable from the user device.

3. The prosthetic foot of claim 2, wherein the different types of human steps include at least two types of human steps selected from the group consisting of: walking on level ground, running on level ground, traversing steps, traversing an incline, and traversing a decline.

4. The prosthetic foot of claim 1, wherein the sensor is positioned directly above the heel member shaft and/or forefoot member shaft so as to be in compressible contact therewith.

5. A system for controlling the movement of a prosthetic foot, the system comprising:
 at least one actuator capable of extending and retracting and in operable contact with a heel member forming a heel portion of the prosthetic foot and/or a forefoot member forming a forefoot portion of the prosthetic foot to cause the heel member shaft and/or forefoot member shaft to translate in a vertical direction;
 at least one sensor positioned so as to detect compressive force applied to the actuator;
 machine readable memory storing a plurality of datasets corresponding to heel member and forefoot member positions during a human step; and
 an electronic controller connected to the sensor and actuator in such a way that the controller receives a signal corresponding to the detected compressive force and adjusts the extension or retraction of the actuator based on at least one of the datasets;
 wherein:
  the heel member is a rigid single piece that extends from an upper end received by an ankle member to a lower end positioned beneath the ankle member; and
  the forefoot member is a rigid single piece that extends from an upper end received by the ankle member to a lower end positioned beneath the ankle member.

6. The system of claim 5, further comprising a user communication device in wireless communication with the electronic controller and wherein the datasets from the plurality of datasets correspond to different types of human steps and a the datasets are independently selectable from the user device.

7. The system of claim 6, wherein the different types of human steps include at least two types of human steps selected from the group consisting of: walking on level ground, running on level ground, traversing steps, traversing an incline, and traversing a decline.

8. The system of claim 5, wherein the sensor is positioned directly above the heel member and/or forefoot member shaft so as to be in compressible contact therewith.

* * * * *